United States Patent [19]

Linden

[11] 4,295,050
[45] Oct. 13, 1981

[54] INSTRUMENT FOR POSITIONING AN X-RAY CAMERA IN DENTAL X-RAY PHOTOGRAPHY

[76] Inventor: Sigurd Linden, Teatergatan 4, Linköping, Sweden

[21] Appl. No.: 121,880

[22] Filed: Feb. 15, 1980

[30] Foreign Application Priority Data

Feb. 27, 1979 [SE] Sweden .................................. 7901788

[51] Int. Cl.³ ............................................... A61B 6/14
[52] U.S. Cl. .................................................... 250/479
[58] Field of Search ........................................ 250/479

[56] References Cited

U.S. PATENT DOCUMENTS 1,404,171 1/1922 Waite .................................. 250/479
1,405,217 1/1922 Houser ............................... 250/479

Primary Examiner—Alfred E. Smith
Assistant Examiner—T. N. Grigsby
Attorney, Agent, or Firm—Frishauf, Holtz, Goodman & Woodward

[57] ABSTRACT

An instrument for use in odontologic X-ray photography comprises an elongated plate-like bite block extending at right angles to an X-ray film support and integrally connected to an arm perpendicular to the longitudinal direction of the block. The instrument also has means for receiving a guide pin facilitating correct orientation of the X-ray camera relatively the film.

6 Claims, 2 Drawing Figures

INSTRUMENT FOR POSITIONING AN X-RAY CAMERA IN DENTAL X-RAY PHOTOGRAPHY

When teeth and surrounding tissues are to be X-rayed it is important correctly to position the X-ray camera. Such a correct positioning involves that two conditions must be satisfied.

The first condition is that the optical axis of the X-ray camera objective must, as accurately as possible, pass through the center of the object to be X-rayed, usually a tooth.

The second condition is that the optical axis of the camera must either be perpendicular to the plane of the film or coincide with the bisector of the angle defined between that plane and the geometric longitudinal axis of the tooth to be X-rayed. The first principle of positioning the camera is referred to as parallel positioning and the second one as the bisecting-angle technique. The latter is used in those cases when, due to the anatomic conditions of the palate, a parallel positioning cannot be used. Independently of which method the dentist elects to use he will invariably, the only exception being X-raying of the front teeth, be confronted with the difficult task of correctly positioning the camera. The corresponding difficulty has the following causes.

When the film has been positioned inside the mouth of the patient, it is, as a rule, not visible to the dentist; in any case he cannot see the side thereof to be exposed. This forces the dentist to position the camera on the basis of sheer estimations both as far as the centering of the camera objective in relation to the object is concerned and with respect to the angular position of the optical axis of the objective in relation to the plane of the film. Should one or both of those estimations deviate more than insignificantly from the correct values, the resulting X-ray picture will, at the best, be difficult to interpret. In many cases it is completely impossible to interpret it, e.g. due to the fact that an adjacent tooth has been partly overlapping the tooth under examination.

Another reason behind the just-mentioned difficulty is the following one. Even if the dentist should succeed in exactly positioning the X-ray camera objective, it still very often happens that the position of the film is changed before exposure thereof has taken place, namely due to the fact that the patient involuntarily makes movements generated by the pressure of the film edges against the inner walls of the mouth cavity.

Instruments of the type above referred to are disclosed in e.g. U.S. Pat. Nos. 3,003,062 and 3,473,026. However, the instrument shown in U.S. Pat. No. 3,003,062 cannot be used when the bisecting-angle technique must be applied. This is very often necessary due to the oral cavity anatomy which in those cases makes it impossible to locate a film parallel to the longitudinal axis of the tooth to be X-rayed. The instrument disclosed in U.S. Pat. No. 3,473,026 is adapted to the bisecting-angle technique but it does not permit the dentist to assure a proper location of the film relatively the tooth or teeth under examination.

Accordingly, it is an object of the present invention to provide a device for positioning a dental X-ray film within the mouth for producing radiographs by the bisecting-angle technique as well as the parallel technique.

Another object of the invention is to provide an instrument of the type above described which makes it possible to locate the film parallel to the tangent of the arc formed by a row of adjacent teeth.

A further object of the invention is to provide an instrument which enables the dentist exactly to reproduce a certain exposure in terms of the location of the film relative to the exposed area.

The above and further objects and advantages of the invention will become apparent from the following description when read in conjunction with the drawing, in which.

Figure 1:
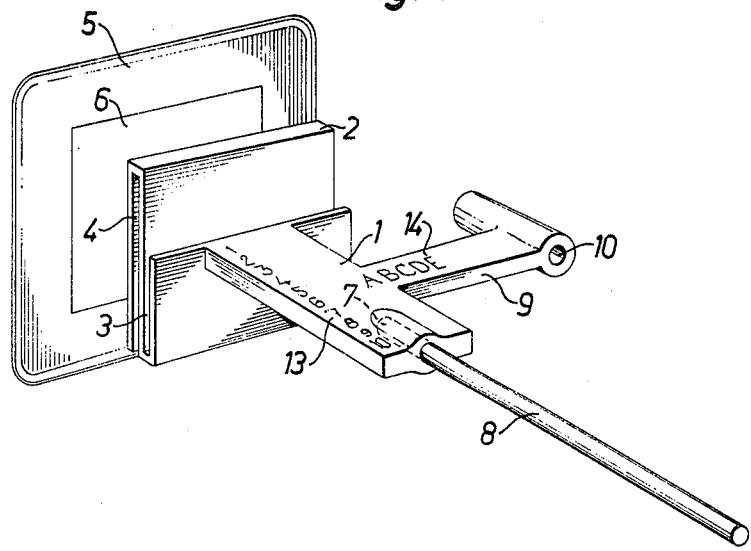
FIG. 1 is a perspective view of the novel instrument.

The main portion of the instrument is a substantially rectangular block 1 made of a synthetic resin material. The inner end of the block is integrally connected to an X-ray film support 2. The term "inner" as used here refers to that part of the instrument which in use is located inside the oral cavity of the patient. According to the embodiment here illustrated support 2 is of generally Z-shaped cross-section so as to define two grooves 3 and 4 adapted to receive a film 5. Thanks to the fact that the horizontal slot of groove 3 is facing upwards and that of groove 4 downwards film 5 may be positioned in different vertical levels with respect to block 1. Alternatively, the film may be mounted on the innermost vertical surface of support 2 by means of tape 6 which is adhesive on both sides. To illustrate this, details 5 and 6 have, in FIG. 1, been shown in an exploded view.

Figure 2:
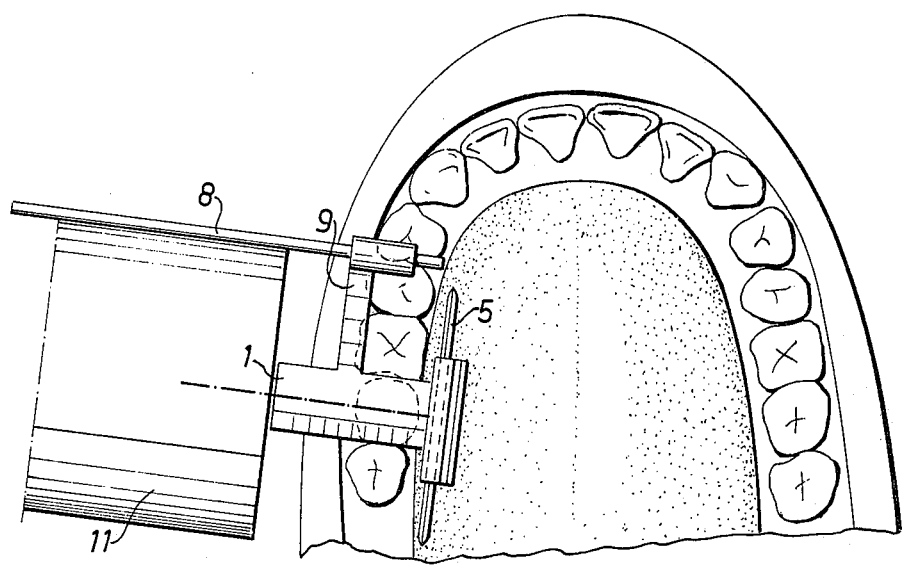
FIG. 2 is a horizontal view diagrammatically illustrating one mode of employment of the instrument.

At its outer end block 1 has a hole 7 extending in the longitudinal direction of the block and adapted detachably to receive a guide pin 8. Block 1 also comprises a cross-wise extending arm 9 which, accordingly, is parallel to the plane of film 5 when carried by support 2 in any of the three positions above mentioned. When the instrument is used, arm 9 is either wholly outside the mouth of the patient or in contact with external sides of two or more teeth, i.e. parallel to the tangent of the teeth arc as shown in FIG. 2.

Arm 9 performs three functions. One of them is that, when it is positioned as just mentioned and as illustrated in FIG. 2, the dentist knows that also film 5 is located parallel to the arc tangent meaning that it is correctly positioned relatively the exposed area.

The second function of arm 9 is that, at its free end, it supports a tubular sleeve the bore 10 of which may receive pin 8. The third function of arm 9 will be described below.

Let it now be assumed that the dentist wants an X-ray picture of a tooth in the lower jaw of his patient. Using his instrument he first inserts a film 5 into groove 4. He then places the instrument in such a position that support 2 with film 5 is located behind the tooth whereas block 1 protrudes laterally outside the mouth through the space between the upper and lower teeth rows. Since the plane of film 9 is perpendicular to the longitudinal axis of block 1 which also is perpendicular to that of arm 9 the dentist may—by placing block 1 so that its longitudinal axis is perpendicular to the longitudinal axes of the teeth and so that arm 9 is parallel to the tangent of the teeth arc as above described and shown in FIG. 2—make sure that film 5 is in a plane that is correctly oriented relatively the area to be exposed. That this condition is fulfilled means that both the arc tangent and the teeth longitudinal axes are parallel with the film plane.

The description just given accordingly relates to X-ray photography using the parallel technique. When the bisecting-angle technique is used, the mode of operation is basically the same, the only difference being the one distinguishing the one method from the other as accounted for above.

Guide pin 8 allows the dentist to check that the optical axis of the camera is parallel to the pin, i.e. perpendicular to the film.

A third mode of exposure is the bite-wing technique which results in a picture covering parts of upper and lower jaw teeth as well as parts of adjacent tissues. When this technique is used, film 5 is generally held by tape 6 as above described. Further, pin 8 is inserted into bore 10 and arm 9 is positioned parallel to the arc tangent.

Pin 8 can also perform a second function. When the crown surfaces of the teeth are not coplanar, compression of block 1 between the upper and lower jaw teeth may tend to tilt the block and hence also the film. Moreover, since bore 10 extends through the arm sleeve, the inner end of pin 8 may be brought into supporting engagement with a tooth beside the block, thereby preventing a tilting movement to occur.

As shown in FIG. 1, block 1 and arm 9 have marking symbols, figures 13 and letters 14, respectively. The purpose thereof is to make it possible, as many times as required, to X-ray exactly the same area. When the first exposure is made the dentist makes a note of the location of block 1 in relation to a suitable tooth by establishing which symbols are close to that tooth. Accordingly, when on a later occasion the block 1 is located in the same position, as determined by means of the symbols, the dentist knows that the corresponding picture will cover exactly the same area as the first one whereby the exposure becomes directly comparable, a feature of very great value in several contexts.

What I claim is:

1. An instrument for positioning the X-ray camera relatively the object and the X-ray film when taking X-ray photographs of teeth or adjacent tissues, comprising a plate-like member which at its one end, during the exposure of the film located inside the object as related to the camera, has a support for holding the film in a plane perpendicular to the longitudinal axis of said plate-like member, the outer end portion of the plate-like member being arranged, during exposure of the film, to be located outside the row of teeth of the patient and having a laterally extending arm-like portion located perpendicularly to the plate-like member and coplanar therewith, means being arranged to receive a guide pin in a position where its longitudinal axis is parallel to that of said plate-like member and said guide pin protrudes outside the oral cavity of the patient, whereby the optical axis of the X-ray camera objective can be positioned relatively said pin and, thence, relatively the film.

2. An instrument as claimed in claim 1, in which the said member has markings arranged in its longitudinal direction.

3. An instrument as claimed in claim 2, in which the arm is provided with markings arranged in its longitudinal direction.

4. An instrument as claimed in claim 1, in which said guide pin is insertable into a hole, the longitudinal axis of which is coaxial with that of the plate-like member and has its orifice in the front end thereof.

5. An instrument as claimed in claim 1, in which, at its free end, said arm has a bore adapted alternatively to receive the guide pin.

6. An instrument as claimed in claim 5, in which said arm bore extends through the arm thereby allowing the guide pin to be longitudinally displaced into contact with the teeth of the patient for the purpose of retaining the instrument in its selected position.

* * * * *